(12) United States Patent
Angov et al.

(10) Patent No.: US 9,683,024 B2
(45) Date of Patent: Jun. 20, 2017

(54) RECOMBINANTLY EXPRESSED PLASMODIUM CELTOS ANTIGEN AND METHODS OF USE THEREOF

(71) Applicants: Evelina Angov, Bethesda, MD (US); Elke Bergmann-Leitner, Kensington, MD (US); Christian Ockenhouse, Chevy Chase, MD (US)

(72) Inventors: Evelina Angov, Bethesda, MD (US); Elke Bergmann-Leitner, Kensington, MD (US); Christian Ockenhouse, Chevy Chase, MD (US)

(73) Assignee: THE UNITED STATES OF AMERICA AS REPRESENTED BY THE SECRETARY OF THE ARMY, Washington, DC (US)

( * ) Notice: Subject to any disclaimer, the term of this patent is extended or adjusted under 35 U.S.C. 154(b) by 0 days.

(21) Appl. No.: 14/803,583

(22) Filed: Jul. 20, 2015

(65) Prior Publication Data
US 2016/0031953 A1    Feb. 4, 2016

Related U.S. Application Data

(62) Division of application No. 13/261,255, filed as application No. PCT/US2009/065568 on Nov. 23, 2009, now Pat. No. 9,120,868.

(60) Provisional application No. 61/117,863, filed on Nov. 25, 2008.

(51) Int. Cl.
*A61K 39/00* (2006.01)
*G01N 33/53* (2006.01)
*C07K 14/445* (2006.01)
*A61K 39/015* (2006.01)
*C07K 16/20* (2006.01)
*G01N 33/569* (2006.01)

(52) U.S. Cl.
CPC .......... *C07K 14/445* (2013.01); *A61K 39/015* (2013.01); *C07K 16/205* (2013.01); *G01N 33/56905* (2013.01); *A61K 39/00* (2013.01); *A61K 2039/55566* (2013.01); *A61K 2039/57* (2013.01); *C07K 2317/76* (2013.01)

(58) Field of Classification Search
None
See application file for complete search history.

(56) References Cited

PUBLICATIONS

Greenspan et al (Nature Biotechnology 7: 936-937, 1999).*
Chothia et al (The EMBO Journal, 1986, 5/4:823-26).*
Mikayama et al. (Nov. 1993, Proc. Natil. Acad. Sci, USA, vol. 90: 10056-10060).
Rudinger et al. (Jun. 1976. Peptide Hormones. Biol. Council. pp. 5-7).
VR Kariu, T et al. (Mol. Microbiol. Jan. 1006, vol. 50, pp. 1369-1379.
Genbank Accession No. BAD97684.1 (Kariu, T. et al. ) Apr. 29, 2005.
Lozano, JM et al. Microbes Infect. May 2007, vol. 9, p. 751-760.
Matuschewski et al., FEBS J. Sep. 2007, vol. 274, pp. 4680-4687.
Garcia, JE et al., Clin. Microbiol. Rev. Oct. 2006, vol. 19, pp. 686-707.

* cited by examiner

*Primary Examiner* — Jennifer Graser
(74) *Attorney, Agent, or Firm* — Elizabeth A. Arwine

(57) ABSTRACT

A synthetic nucleotide, which transcribes as the cell-traversal protein for ookinetes and sporozoites (CelTOS) antigen of Malaria *Plasmodium*, and methods of use thereof.

10 Claims, 15 Drawing Sheets

Figure 7:
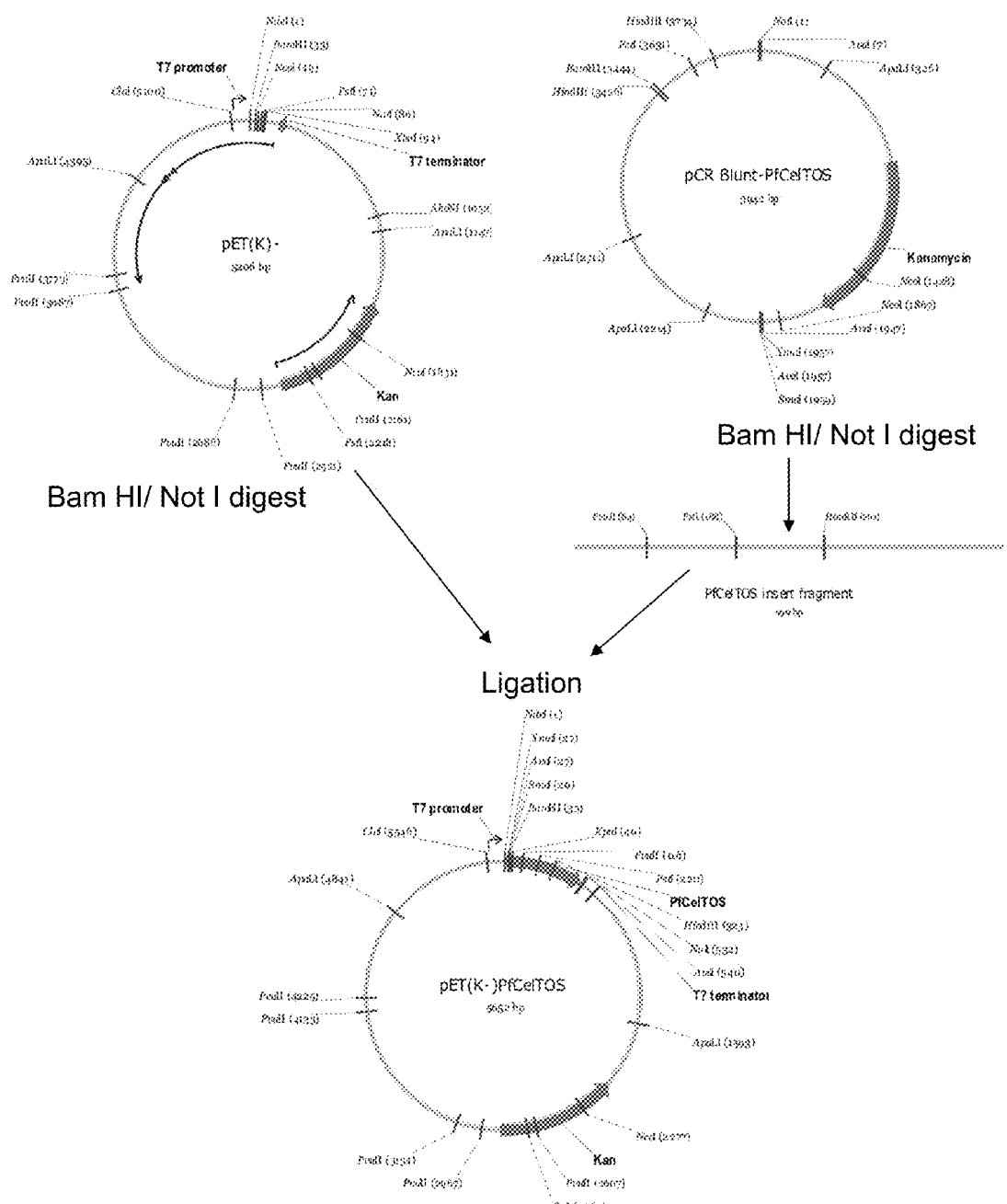
Figure 8:
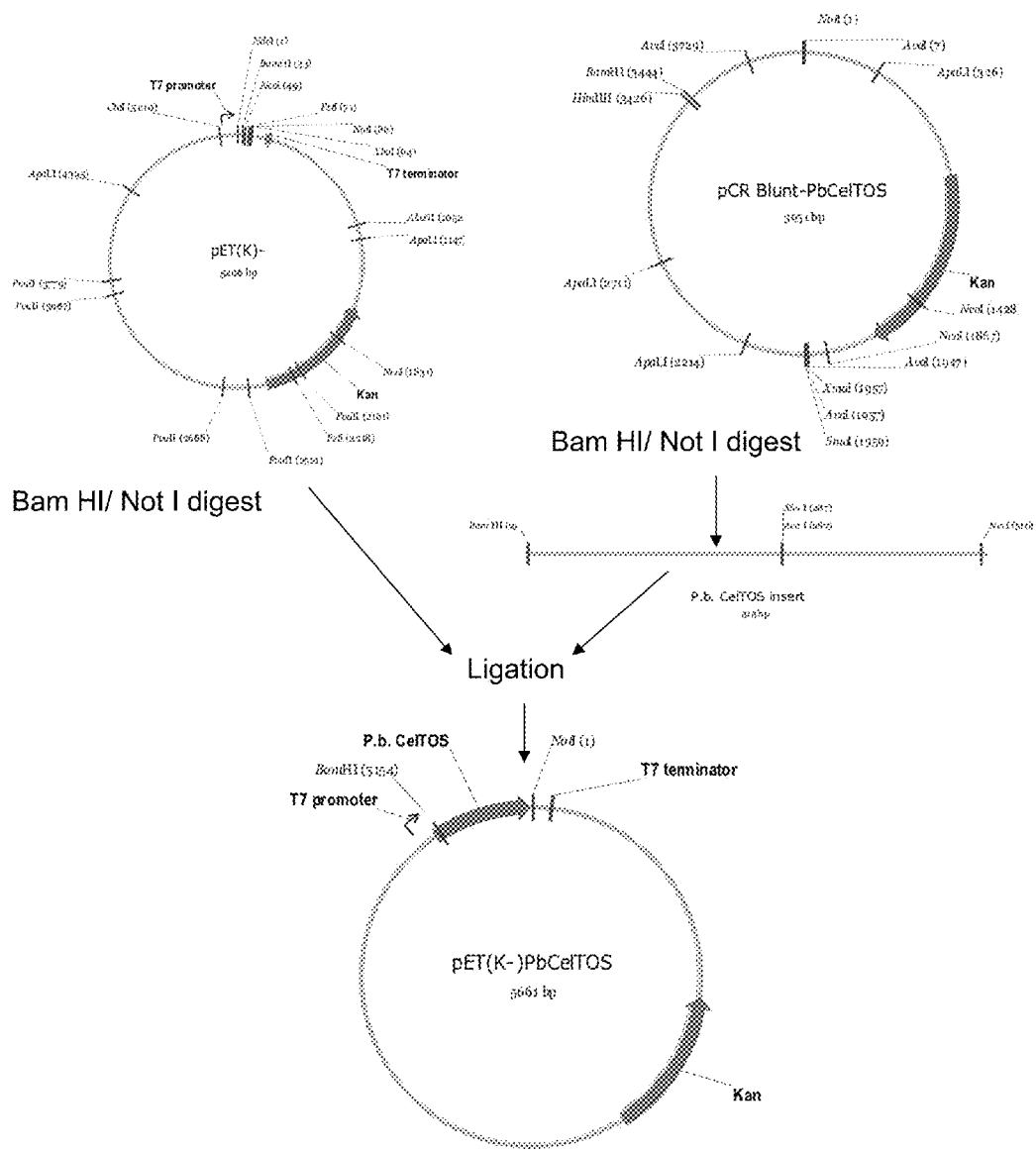
Figure 9:
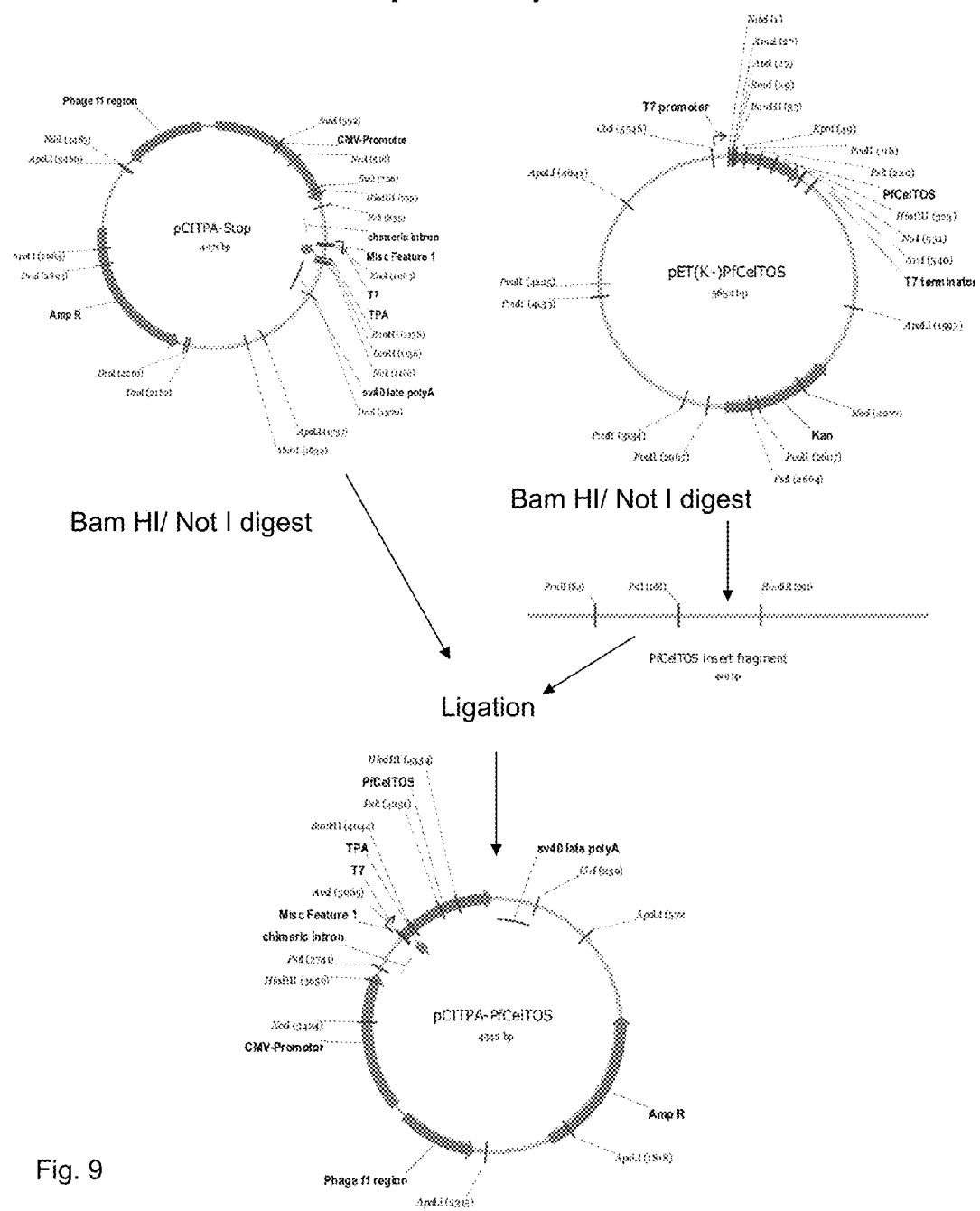
Figure 10:
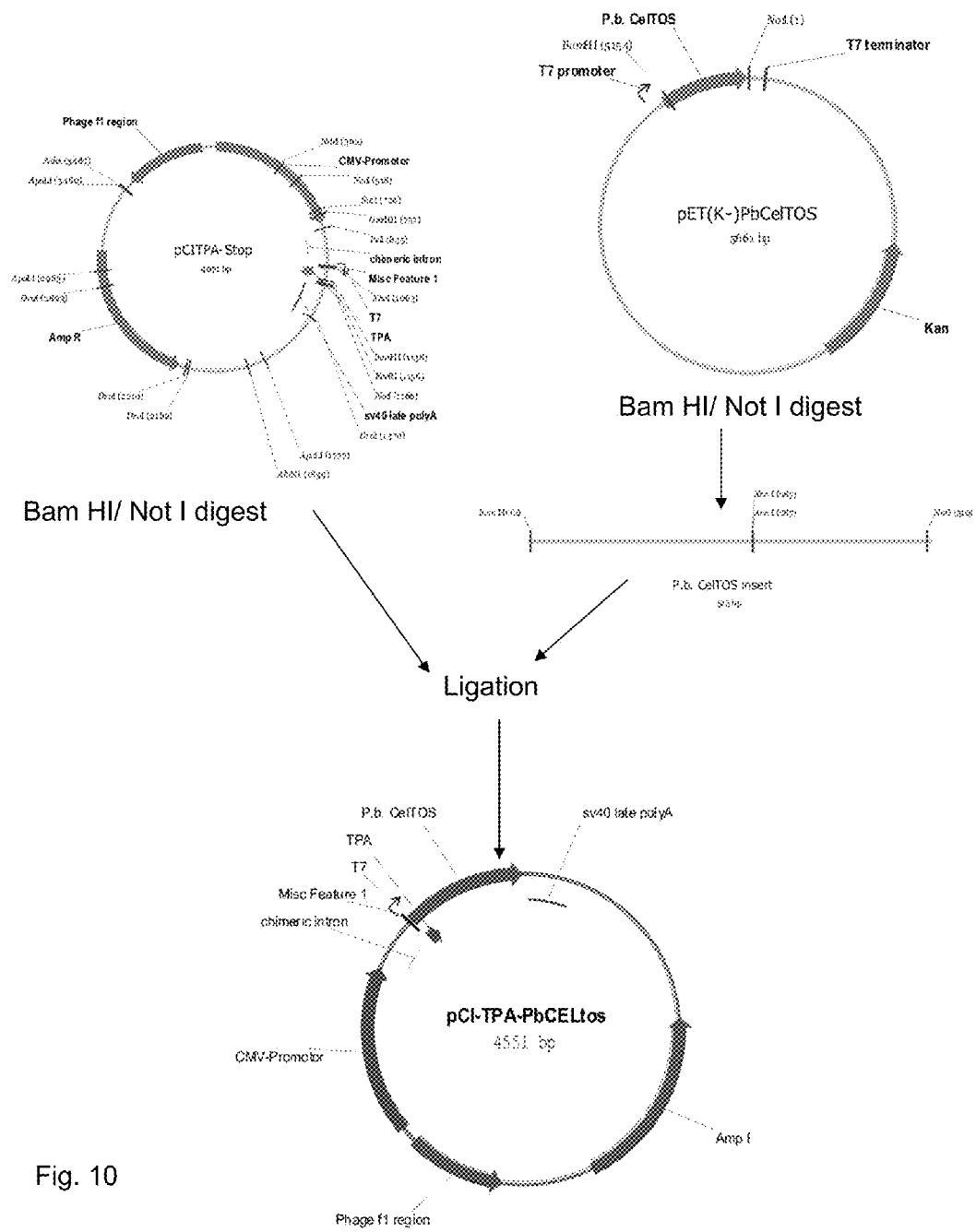

| Pilot Study 1: | BalbC Mice | | | | | | |
|---|---|---|---|---|---|---|---|
| | | | Cumulative Results from Blood Smears | | | | Final |
| Protein Immunization | Dose (µg) | N | 22-May P.berghei infected | 24-May P.berghei infected | 26-May P.berghei infected | 26-May P.berghei infected | 30-May P.berghei infected |
| Pf CelTOS/ISA 720 | 1 | 5 | 3 | 3 | 3 | 3 | 3 |
| | 10 | 5 | 4 | 5 | 5 | 5 | 5 |
| PbCelTOS/ISA 720 | 1 | 5 | 3 | 3 | 3 | 3 | 3 |
| | 10 | 5 | 2 | 2 | 2 | 2 | 2 |
| MONTANIDE TM Alone | | 5 | 4 | 5 | 5 | 5 | 5 |
| Challenge with total of 4000 sporozoites, subcutaneously, at 2 sites inguinal area (100 µl vol. ea.) | | | | | | | |

FIG. 1

| Study 2: | ICR Mice | | | | | | |
|---|---|---|---|---|---|---|---|
| | | | P. berghei infected | P. berghei infected | P. berghei infected | P. berghei infected | P. berghei infected |
| Groups | Dose µg | N | Day 6 | Day 8 | Day 11 | Day 14 | Final |
| Pb CelTOS-Gene gun | | 10 | 7/10 | 8/10 | | 8/10 | 8/10 |
| Pf CelTOS-Gene gun | | 10 | 5/9 | 7/9 | | 7/9 | 7/9 |
| pcDNA (empty vector) | | 10 | 9/10 | 10/10 | | 10/10 | 10/10 |
| Pb CSP-A, gene gun | | 10 | 4/10 | 5/10 | | 5/10 | 5/10 |
| Pb CelTOS/ISA 720 | 10 | 10 | 5/10 | 8/10 | | 8/10 | 8/10 |
| Pb CelTOS/ISA 720 | 1 | 10 | 9/10 | 9/10 | | 9/10 | 9/10 |
| Pf CelTOS/ISA 720 | 10 | 10 | 2/9 | 3/9 | | 3/9 | 3/9 |
| Pf CelTOS/ISA 720 | 1 | 10 | 8/10 | 10/10 | | 10/10 | 10/10 |
| MONTANIDE TM alone | | 10 | 8/9 | 8/9 | | 8/9 | 8/9 |
| Pb CSP-TR/ISA 720 | 1 | 10 | 3/10 | 3/10 | | 3/10 | 3/10 |
| Challenge with total of 4000 sporozoites, subcutaneously, at 2 sites inguinal area (100 µl vol. ea.) | | | | | | | |

FIG. 2

Study 2:   BalbC Mice

| Groups | Dose μg | N | P. berghei infected Day 6 | P. berghei infected Day 8 | P. berghei infected Day 11 | P. berghei infected Day 14 | P. berghei infected Final |
|---|---|---|---|---|---|---|---|
| PbCelTOS/ISA 720(AG) | 1 | 5 | 2/5 | 2/5 | | 2/5 | 2/5 |
| PbCelTOS/ISA 720 (VG) | 1 | 5 | 1/5 | 1/5 | | 1/5 | 1/5 |
| PbCSP-TR/ISA 720 | 1 | 10 | 0/10 | 0/10 | | 0/10 | 0/10 |
| MONTANIDE TM alone | | 5 | 5/5 | 5/5 | | 5/5 | 5/5 |
| pcDNA (empty vector) | | | 7/10 | 8/10 | | 8/10 | 8/10 |
| Pb CSP-A, gene gun | | | 0/10 | 0/10 | | 0/10 | 0/10 |
| Challenge with total of 4000 sporozoites, subcutaneously, at 2 sites inguinal area (100 μl vol. ea.) | | | | | | | |

FIG. 3

ATGGCACACCATCATCATCATCATCCCGGGGGATCCGGTTCTGGTACCTTTCGTGGCAAC
AATGGCCATAACAGCAGCAGCAGCTTATACAACGGCTCGCAGTTCATTGAACAGCTGAAC
AATTCTTTCACTAGCGCTTTCCTCGAAAGCCAGAGCATGAACAAGATTGGCGACGACCTG
GCTGAGACGATCAGCAACGAACTGGTCTCTGTTCTGCAGAAAAACAGCCCAACGTTCCTG
GAAAGCTCGTTCGACATAAAAAGCGAAGTTAAAAAACATGCTAAAAGCATGCTGAAGGAA
CTGATAAAAGTTGGCCTCCCAAGCTTTGAAAACTTAGTTGCTGAAAACGTTAAACCACCA
AAAGTCGATCCAGCTACCTACGGCATCATCGTTCCAGTTCTGACCAGCCTGTTCAACAAG
GTTGAAACCGCTGTTGGCGCCAAAGTTAGCGACGAGATCTGGAACTATAACAGCCCAGAT
GTCAGCGAATCTGAAGAATCTCTGAGCGACGACTTCTTTGACTGATAA

FIG. 4

```
MAHHHHHHPG GSGSGTFRGN NGHNSSSSLY NGSQFIEQLN NSFTSAFLES
QSMNKIGDDL AETISNELVS VLQKNSPTFL ESSFDIKSEV KKHAKSMLKE
LIKVGLPSFE NLVAENVKPP KVDPATYGII VPVLTSLFNK VETAVGAKVS
DEIWNYNSPD  VSESEESLSD DFFD
```

FIG. 5

| | | | | | | | | | | |
|---|---|---|---|---|---|---|---|---|---|---|
| 1 - | ATG | GCA | CAC | CAT | CAT | CAT | CAT | CCC | GGG | GGA | TCC | GGT | TCT | GGT | ACC | TTT | CGT | GGC | AAC | - 60 |
| 1 - | M | A | H | H | H | H | H | P | G | G | S | G | S | G | T | F | R | G | N | - 20 |
| 61 - | AAT | GGC | CAT | AAC | AGC | AGC | AGC | TTA | TAC | GGC | AAC | TCG | CAG | TTC | ATT | GAA | CAG | CTG | AAC | - 120 |
| 21 - | N | G | H | N | S | S | S | L | Y | G | N | S | Q | F | I | E | Q | L | N | - 40 |
| 121 - | AAT | TCT | TTC | ACT | AGC | ATC | AGC | GCT | TTC | CTC | GAA | AGC | CAG | AGC | ATG | AAC | AAG | ATT | GGC | GAC | GAC | CTG | - 180 |
| 41 - | N | S | F | T | S | I | S | A | F | L | E | S | Q | S | M | N | K | I | G | D | D | L | - 60 |
| 181 - | GCT | GAG | ACG | ATC | AGC | AAC | GAA | CTG | GTC | TCT | GTT | CTG | CAG | AAA | AAC | AGC | CCA | ACG | TTC | CTG | - 240 |
| 61 - | A | E | T | I | S | N | E | L | V | S | V | L | Q | K | N | S | P | T | F | L | - 80 |
| 241 - | GAA | AGC | TCG | TTC | GAC | ATA | AAA | AGC | GAA | GTT | AAA | CAT | GCT | AAA | AGC | ATG | CTG | AAG | GAA | - 300 |
| 81 - | E | S | S | F | D | I | K | S | E | V | K | H | A | K | S | M | L | K | E | - 100 |
| 301 - | CTG | ATA | AAA | GTT | GGC | CTC | CCA | AGC | TTT | GAA | AAC | TTA | GTT | GCT | GAA | AAC | GTT | AAA | CCA | CCA | - 360 |
| 101 - | L | I | K | V | G | L | P | S | F | E | N | L | V | A | E | N | V | K | P | P | - 120 |
| 361 - | AAA | GTC | GAT | CCA | GCT | ACC | TAC | GGC | ATC | ATC | GTT | CCA | GTT | CTG | ACC | CTG | TTC | AAC | AAG | - 420 |
| 121 - | K | V | D | P | A | T | Y | G | I | I | V | P | V | L | T | L | F | N | K | - 140 |
| 421 - | GTT | GAA | ACC | GCT | GTT | GGC | GCC | AAA | GTT | AGC | GAC | GAG | ATC | TGG | AAC | TAT | AAC | AGC | CCA | GAT | - 480 |
| 141 - | V | E | T | A | V | G | A | K | V | S | D | E | I | W | N | Y | N | S | P | D | - 160 |
| 481 - | GTC | AGC | GAA | TCT | GAA | GAA | TCT | CTG | AGC | GAC | GAC | TTC | TTT | GAC | TGA | TAA | - 528 |
| 161 - | V | S | E | S | E | E | S | L | S | D | D | F | F | D | * | * | X | - 180 |

FIG. 6

```
METAHHHHPG GSGSGTFRGN NGHNSSSSLY NGSQFIEQLN NSFTSAFLES
QSMNKIGDDL AETISNELVS VLQKNSPTFL ESSFDIKSEV KKHAKSMLKE
LIKVGLPSFE NLVAENVKPP KVDPATYGII VPVLTSLFNK VETAVGAKVS
DEIWNYNSPD  VSESEESLSD DFFD
```

FIG. 12

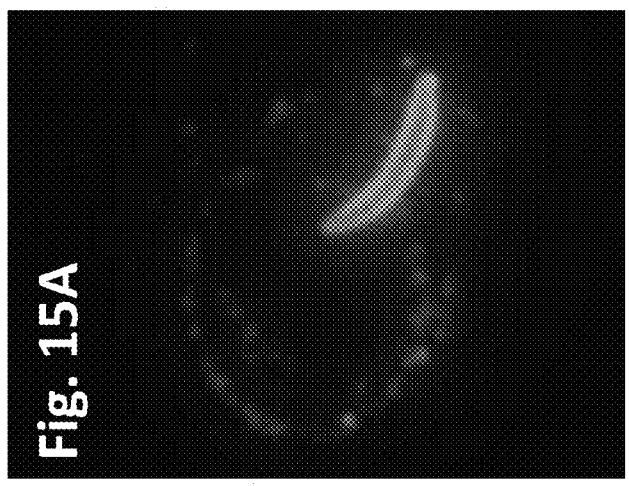
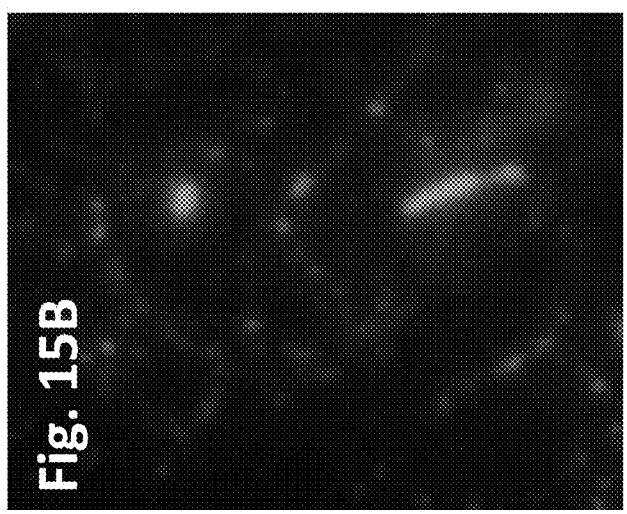
Fig. 15

SEQUENCE LISTING

```
<160> NUMBER OF SEQ ID NOS: 4

<210> SEQ ID NO 1
<211> LENGTH: 528
<212> TYPE: DNA
<213> ORGANISM: artificial
<220> FEATURE:
<223> OTHER INFORMATION: Plasmodium falciparum CelTOS nucleotide
      sequence optomized by codon harmonization for expression

<400> SEQUENCE: 1
atggcacacc atcatcatca tcatcccggg ggatccggtt ctggtacctt tcgtggcaac      60
aatggccata acagcagcag cagcttatac aacggctcgc agttcattga acagctgaac     120
aattctttca ctagcgcttt cctcgaaagc cagagcatga caagattgg cgacgacctg      180 gctgagacga tcagcaacga actggtctct gttctgcaga aaaacagccc aacgttcctg     240
gaaagctcgt tcgacataaa aagcgaagtt aaaaaacatg ctaaaagcat gctgaaggaa     300
ctgataaaag ttggcctccc aagctttgaa aacttagttg ctgaaaacgt taaaccacca     360
aaagtcgatc cagctaccta cggcatcatc gttccagttc tgaccagcct gttcaacaag     420
gttgaaaccg ctgttggcgc caaagttagc gacgagatct ggaactataa cagcccagat     480
gtcagcgaat ctgaagaatc tctgagcgac gacttctttg actgataa                  528

<210> SEQ ID NO 2
<211> LENGTH: 174
<212> TYPE: PRT
<213> ORGANISM: artificial
<220> FEATURE:
<223> OTHER INFORMATION: Plasmodium falciparum CelTOS peptide sequence
      after codon optimization

<400> SEQUENCE: 2

Met Ala His His His His His His Pro Gly Gly Ser Gly Ser Gly Thr
1               5                   10                  15
```

```
Phe Arg Gly Asn Asn Gly His Asn Ser Ser Ser Leu Tyr Asn Gly
            20                  25                  30

Ser Gln Phe Ile Glu Gln Leu Asn Asn Ser Phe Thr Ser Ala Phe Leu
        35                  40                  45

Glu Ser Gln Ser Met Asn Lys Ile Gly Asp Asp Leu Ala Glu Thr Ile
50                  55                  60

Ser Asn Glu Leu Val Ser Val Leu Gln Lys Asn Ser Pro Thr Phe Leu
65                  70                  75                  80

Glu Ser Ser Phe Asp Ile Lys Ser Glu Val Lys Lys His Ala Lys Ser
                85                  90                  95

Met Leu Lys Glu Leu Ile Lys Val Gly Leu Pro Ser Phe Glu Asn Leu
            100                 105                 110

Val Ala Glu Asn Val Lys Pro Pro Lys Val Asp Pro Ala Thr Tyr Gly
            115                 120                 125

Ile Ile Val Pro Val Leu Thr Ser Leu Phe Asn Lys Val Glu Thr Ala
            130                 135                 140

Val Gly Ala Lys Val Ser Asp Glu Ile Trp Asn Tyr Asn Ser Pro Asp
145                 150                 155                 160

Val Ser Glu Ser Glu Glu Ser Leu Ser Asp Asp Phe Phe Asp
                165                 170

<210> SEQ ID NO 3
<211> LENGTH: 174
<212> TYPE: PRT
<213> ORGANISM: Plasmodium falciparum

<400> SEQUENCE: 3

Met Glu Thr Ala His His His Pro Gly Gly Ser Gly Ser Gly Thr
1               5                   10                  15

Phe Arg Gly Asn Asn Gly His Asn Ser Ser Ser Leu Tyr Asn Gly
            20                  25                  30

Ser Gln Phe Ile Glu Gln Leu Asn Asn Ser Phe Thr Ser Ala Phe Leu
        35                  40                  45

Glu Ser Gln Ser Met Asn Lys Ile Gly Asp Asp Leu Ala Glu Thr Ile
50                  55                  60

Ser Asn Glu Leu Val Ser Val Leu Gln Lys Asn Ser Pro Thr Phe Leu
65                  70                  75                  80

Glu Ser Ser Phe Asp Ile Lys Ser Glu Val Lys Lys His Ala Lys Ser
                85                  90                  95

Met Leu Lys Glu Leu Ile Lys Val Gly Leu Pro Ser Phe Glu Asn Leu
            100                 105                 110

Val Ala Glu Asn Val Lys Pro Pro Lys Val Asp Pro Ala Thr Tyr Gly
            115                 120                 125

Ile Ile Val Pro Val Leu Thr Ser Leu Phe Asn Lys Val Glu Thr Ala
            130                 135                 140

Val Gly Ala Lys Val Ser Asp Glu Ile Trp Asn Tyr Asn Ser Pro Asp
145                 150                 155                 160

Val Ser Glu Ser Glu Glu Ser Leu Ser Asp Asp Phe Phe Asp
                165                 170

<210> SEQ ID NO 4
<211> LENGTH: 182
<212> TYPE: PRT
<213> ORGANISM: Plasmodium falciparum

<400> SEQUENCE: 4
```

-continued

```
Met Asn Ala Leu Arg Arg Leu Pro Val Ile Cys Ser Phe Leu Val Phe
1               5                   10                  15

Leu Val Phe Ser Asn Val Leu Cys Phe Arg Gly Asn Asn Gly His Asn
            20                  25                  30

Ser Ser Ser Ser Leu Tyr Asn Gly Ser Gln Phe Ile Glu Gln Leu Asn
        35                  40                  45

Asn Ser Phe Thr Ser Ala Phe Leu Glu Ser Gln Ser Met Asn Lys Ile
    50                  55                  60

Gly Asp Asp Leu Ala Glu Thr Ile Ser Asn Glu Leu Val Ser Val Leu
65                  70                  75                  80

Gln Lys Asn Ser Pro Thr Phe Leu Glu Ser Ser Phe Asp Ile Lys Ser
                85                  90                  95

Glu Val Lys Lys His Ala Lys Ser Met Leu Lys Glu Leu Ile Lys Val
            100                 105                 110

Gly Leu Pro Ser Phe Glu Asn Leu Val Ala Glu Asn Val Lys Pro Pro
        115                 120                 125

Lys Val Asp Pro Ala Thr Tyr Gly Ile Ile Val Pro Val Leu Thr Ser
    130                 135                 140

Leu Phe Asn Lys Val Glu Thr Ala Val Gly Ala Lys Val Ser Asp Glu
145                 150                 155                 160

Ile Trp Asn Tyr Asn Ser Pro Asp Val Ser Glu Ser Glu Glu Ser Leu
                165                 170                 175

Ser Asp Asp Phe Phe Asp
            180
```

RECOMBINANTLY EXPRESSED PLASMODIUM CELTOS ANTIGEN AND METHODS OF USE THEREOF

REFERENCE TO RELATED APPLICATIONS

This application claims the benefit of U.S. Provisional Application No. 61/117,863 filed Nov. 25, 2008. The entirety of which is specifically incorporated by reference herein.

RIGHTS IN THE INVENTION

This invention was made with support from the United States Government and, specifically, the Walter Reed Army Institute of Research and, accordingly, the United States government has certain rights in this invention.

FIELD AND BACKGROUND OF THE INVENTION

The present invention relates generally to fields of medicine and biotechnology. More particularly, the invention relates to the manufacture and use of a vaccine incorporating recombinantly expressed Plasmodium cell-traversal protein for ookinetes and sporozoites (CelTOS) to induce pre-erythrocytic immunity against malaria.

Malaria currently represents one of the most prevalent infections in tropical and subtropical areas throughout the world. Per year, malaria infections lead to severe illnesses in hundreds of million individuals worldwide, while it kills 1 to 3 million people, primarily in developing and emerging countries every year. The widespread occurrence and elevated incidence of malaria are a consequence of the increasing numbers of drug-resistant parasites and insecticide-resistant parasite vectors. Other factors include environmental and climatic changes, civil disturbances, and increased mobility of populations.

Malaria is caused by the mosquito-borne hematoprotozoan parasites belonging to the genus Plasmodium. Four species of Plasmodium protozoa (P. falciparum, P. vivax, P. ovale and P. malariae) are responsible for the disease in humans; many others cause disease in animals, such as P. yoelii and P. berghei in mice. P. falciparum accounts for the majority of infections and is the most lethal type ("tropical malaria"). Malaria parasites have a life cycle consisting of several stages. Each stage is able to induce specific immune responses directed against the corresponding occurring stage-specific antigens.

Malaria parasites are transmitted to man by several species of female Anopheles mosquitoes. Infected mosquitoes inject the "sporozoite" form of the malaria parasite into the mammalian bloodstream. Sporozoites remain for a few minutes in the circulation before invading hepatocytes. At this stage, the parasite is located in the extra-cellular environment and is exposed to antibody attack, mainly directed to the "circumsporozoite" (CS) protein (CSP), a major component of the sporozoite surface. Once in the liver, the parasites replicate and develop into so-called "schizonts." These schizonts occur in a ratio of up to 20,000 per infected cell. During this intra-cellular stage of the parasite, main players of the host immune response are T-lymphocytes, especially CD8+ T-lymphocytes (Bruna-Romero, Gonzalez-Aseguinolaza et al. 2001). After about one week of liver infection, thousands of so-called "merozoites" are released into the bloodstream and enter red blood cells, becoming targets of antibody-mediated immune response and T-cell secreted cytokines. After invading erythrocytes, the merozoites undergo several stages of replication and transform into so-called "trophozoites" and into schizonts and merozoites, which can infect new red blood cells. This stage is associated with overt clinical disease. A limited amount of trophozoites may evolve into "gametocytes," which is the parasite's sexual stage. When susceptible mosquitoes ingest erythrocytes, gametocytes are released from the erythrocytes, resulting in several male gametocytes and one female gametocyte. The fertilization of these gametes leads to zygote formation and subsequent transformation into ookinetes, then into oocysts, and finally into salivary gland sporozoites.

The malarial protein designated CelTOS, for cell-traversal protein for ookinetes and sporozoites, from Plasmodium berghei has previously been shown to mediate malarial invasion of both vertebrate and mosquito host cells and is required for establishing their successful infections (Kariu, Ishino et al. 2006). In the vertebrate host, Plasmodium sporozoites traverse to hepatocytes via a complex passage initiating at the dermis and traversing through cellular barriers in the skin and the liver sinusoid. Therefore, the Induction of immunity targeted to molecules involved in sporozoite motility and migration into hepatocytes may lead to nonproductive and/or reduced hepatocytic infection.

Malaria-naïve individuals do not possess partial immunity developed over life-long exposures. The current malaria vaccines being tested are insufficient to induce appropriate long lived memory responses. Therefore the need exists for an efficacious, long-term, pre-erythrocytic stage malaria vaccine to be used alone or in combination with alternate treatment strategies.

SUMMARY OF THE INVENTION

Immunization with a CelTOS vaccine could mimic the development of immunity from natural malaria exposures. The development of an efficacious pre-erythrocytic stage malaria vaccine from the Plasmodium protein CelTOS, (cell traversal protein for ookinetes and sporozoites) has the potential to protect human populations in malaria endemic regions. Vaccination with a pre-erythrocytic stage vaccine reduces or eliminates the traversal of infective sporozoites through cells required for infection of liver cells and thus protect against infection and/or reduce the severity of the Malarial disease The mechanism of protection induced by a pre-erythrocytic stage malaria vaccine would be mediated by the development of specific protective antibodies to proteins on the parasite surface and block the traversal of the sporozoite through cells leading to productive infection. The putative mode of action of these antibodies is to bind the surface of the sporozoites and block their ability to associate with and invade cells involved in hepatocyte infection. The effect of blocking this process would be to reduce the potential amplification of parasites in the liver and thus reduce parasitic load.

Recombinant proteins expressed in E. coli can yield high levels of properly folded soluble protein. Development of a recombinant protein PfCelTOS vaccine can be used in combination with other candidate malaria vaccines, from either pre-erythrocytic stages or blood stages. These stage and combination antigen vaccine approaches may lead to the induction of a broader immune response.

One embodiment of the invention utilizes CelTOS as target antigen for a pre-erythrocytic vaccine. An alternate embodiment of the invention is a well expressed recombinant *Plasmodium* CelTOS protein utilizing codon harmonization. The technique for codon harmonization is disclosed in Published U.S. application Ser. No. 10/677,641 to Kincaid et al. which is incorporated by referenced in its entirety herein.

Another embodiment of the invention is a recombinant subunit CeltTOS malaria vaccine expressed in *E. coli* utilizing a soluble, high yielding purification process.

Yet another embodiment of the invention is a method of inducing antibodies induced against CelTOS that are reactive against malarial sporozoites to prevent liver stage infection.

A alternate embodiment of the invention is a method of inducing antibodies induced against CelTOS that are reactive against malarial ookinetes in the mosquito midgut preventing development of infectious salivary gland sporozoites Another embodiment of the invention is a pre-erythrocytic stage malaria vaccine to be used alone or in combination with alternate treatment strategies.

A further embodiment of the invention is as a pre-erythrocytic biomarker for exposure to malaria.

Another embodiment of the invention to use CelTOS antigens as a reagent for stimulating cells, T cells and B cells.

It is yet another embodiment of the invention to use CelTOS antigens as a reagent for evaluating antibody responses by ELISA, Luminex, or similar technologies well known in the art.

An additional embodiment of the invention is as a reagent used to develop monoclonal antibodies against the target *Plasmodium* parasite. Such monoclonal antibodies can potentially be used for passive immunotherapy.

Another embodiment of the invention is as a reagent to study protein folding and structure.

The various features of novelty that characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the drawings:

FIG. 1 is a table showing *P. berghei* challenge and protection results in BalbC Mice. BalbC mice were immunized subcutaneously in the inguinal area at 3 week intervals with either a low (1 μg) dose or high dose (10 μg) of recombinant protein in a vaccine adjuvant such as MONTANIDE™ ISA 720 (A.L.A. Intermountain, 3725 E. Washington Street, Phoenix, Ariz. 85034). Mice were challenged with a total of 4000 *P. berghei* sporozites, subcutaneously at 2 sites in the inguinal area. Blood smears were made on Day 6, Day 8, Day 10, Day 12 and Day 14 post challenge to determine infectivity. Results are shown as number of mice infected out of 5 mice per group.

FIG. 2 is a table showing *P. berghei* challenge and protection results in ICR mice immunized subcutaneously with a recombinant protein and a vaccine adjuvant. ICR mice were immunized subcutaneously, inguinal area, 3 week intervals with a low (1 μg) dose or high dose (10 μg) of recombinant protein and a vaccine adjuvant such as MONTANIDE™ ISA 720 (A.L.A. Intermountain, 3725 E. Washington Street, Phoenix, Ariz. 85034). Mice were challenged with *P. berghei* sporozoites, subcutaneously at 2 sites in the inguinal area. Blood smears were made on Day 6, Day 8, Day 10, Day 12 and Day 14 post challenge to determine infectivity. Results are Number of Mice that became infected over the total.

FIG. 3 is a table showing *P. berghei* challenge and protection results in BalbC mice immunized subcutaneously with a recombinant protein and a vaccine adjuvant. BalbC mice were immunized subcutaneously, inguinal area, 3 week intervals with a low (1 ug) dose of high dose (10 ug) of recombinant protein and a vaccine adjuvant such as MONTANIDE™ ISA 720 (A.L.A. Intermountain, 3725 E. Washington Street, Phoenix, Ariz. 85034). Mice were challenged with *P. berghei* sporozoites, subcutaneously at 2 sites in the inguinal area. Blood smears were made on Day 6, Day 8, Day 1, Day 12 and Day 14 post challenge to determine infectivity. Results are Number of Mice that became infected over the total.

FIG. 4 is a *Plasmodium falciparum* CelTOS nucleotide sequence which was optimized by codon harmonization for expression (SEQ ID NO:1)

FIG. 5 is a *Plasmodium falciparum* CelTOS peptide sequence (SEQ ID. NO. 2)

FIG. 6 is a translation map for the 528 residue sequence of *Plasmodium falciparum* CelTOS (PfCelTOS) (SEQ ID NO:1).

FIG. 7 is a diagram showing the construction of the pET(K-)PfCelTOS plasmid.

FIG. 8 is a diagram showing the construction of the pET(K-)PbCelTOS plasmid.

FIG. 9 is a diagram showing the construction of the pCI-TPA-PfCelTOS plasmid.

FIG. 10 is a diagram showing the construction of the pCI-TPA-PbCelTOS plasmid.

FIG. 11A is a photograph of an electrophoresis gel panel showing recombinant PbCelTOS and PfCelTOS expression profiles in *E. Coli* Lysates.

FIG. 11B is a photograph of an electrophoresis gel panel showing recombinant PbCelTOS and PfCelTOS expression profiles in *E. Coli* Lysates probed with mAb against His-tag.

FIG. 12 is a sequence generated by the NetNGlyc 1.0 Server at the Technical University of Denmark. The NetNglyc server predicts N-Glycosylation sites in human proteins using artificial neural networks that examine the sequence context of Asn-Xaa-Ser/Thr sequons. See Prediction of N-glycosylation sites in human proteins. R. Gupta, E. Jung and S. Brunak. In preparation, 2004 incorporated herein by reference in its entirety. Asn-Xaa-Ser/Thr sequons in the sequence are in bold. Asparagines predicted to be N-glycosylated are underlined. Proteins without signal peptides are unlikely to be exposed to the N-glycosylation machinery and thus may not be glycosylated (in vivo) even though they contain potential motifs. (SEQ. ID. NO. 3).

FIG. 13 is a summary ELISA Antibody from pooled groups of Study No. 1.

FIG. 14A is a photograph of an electrophoresis gel showing high soluble protein yields of the PbCelTOS construct.

FIG. 14B is a photograph of an electrophoresis gel showing high soluble protein yields of the PfCelTOS construct.

FIG. 15A is photograph of *Plasmodium falciparum* sporozoites pre-incubated with control serum and immunofluorescent treatment.

FIG. 15B is a photograph of *Plasmodium falciparum* sporozoites pre-incubated with a PfCSP-specific monoclonal antibody and immunofluorescent treatment.

FIG. 15C is a photograph of *Plasmodium falciparum* sporozoites pre-incubased with PfCelTOS-specific antiserum and immunofluorescent treatment.

DESCRIPTION OF THE PREFERRED EMBODIMENTS

The practice of the present invention will employ, unless otherwise indicated, conventional methods of chemistry, biochemistry, recombinant DNA techniques and immunology, within the skill of the art. Such techniques are explained fully in the literature. See, e.g., (Sambrook and Russell 2006); DNA Cloning, Vols. I and II (Glover and Hames 1994); Oligonucleotide Synthesis (M. (Gait 1984); Nucleic Acid Hybridization; (Perbal 1988), Practical Guide to Molecular Cloning.

All publications, patents and patent applications cited herein, whether supra or infra, are hereby incorporated by reference in their entirety.

It must be noted that, as used in this specification and the appended claims, the singular forms "a", "an" and "the" include plural referents unless the content clearly dictates otherwise. Thus, for example, reference to an antigen includes a mixture of two or more antigens, and the like.

The following amino acid abbreviations are used throughout the text:

Alanine: Ala (A) Arginine: Arg (R) Asparagine: Asn (N) Aspartic acid: Asp (D) Cysteine: Cys (C) Glutamine: Gln (Q) Glutamic acid; Glu (E) Glycine; Gly (G) Histidine: His (H) Isoleucine: Ile (I) Leucine: Leu (L) Lysine: Lys (K) Methionine: Met (M) Phenylalanine: Phe (F) Proline: Pro (P) Serine: Ser (S) Threonine: Thr (T) Tryptophan: Trp (W) Tyrosine: Tyr (Y) Valine: Val (V)

DEFINITIONS

In describing the present invention, the following terms will be employed, and are intended to be defined as indicated below.

The terms polypeptide and protein refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include post-expression modifications of the polypeptide, for example, glycosylation, acetylation, phosphorylation and the like.

For purposes of the present invention, the polypeptide expressed by the coding sequence may be one useful in a vaccine, therapeutic or diagnostic and may be derived from any of several known viruses, bacteria, parasites and fungi, as well as any of the various tumor antigens. Alternatively, the expressed polypeptide may be a therapeutic hormone, a transcription or translation mediator, an enzyme, an intermediate in a metabolic pathway, an immunomodulator, and the like.

Furthermore, for purposes of the present invention, a polypeptide refers to a protein which includes modifications, such as deletions, additions and substitutions (generally conservative in nature), to the native sequence, so long as the protein maintains the desired activity. These modifications may be deliberate, as through site-directed mutagenesis, or may be serendipitous, such as through mutations of hosts which produce the proteins or errors due to PCR amplification.

A coding sequence or a sequence which encodes a selected polypeptide, is a nucleic acid molecule which is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, cDNA from viral, procaryotic or eucaryotic mRNA, genomic DNA sequences from viral (e.g. DNA viruses and retroviruses) or procaryotic DNA, and synthetic DNA sequences. A transcription termination sequence may be located 3' to the coding sequence.

A nucleic acid molecule can include both double- and single-stranded sequences and refers to, but is not limited to, cDNA from viral, procaryotic or eucaryotic mRNA, genomic DNA sequences from viral (e.g. DNA viruses and retroviruses) or procaryotic DNA, and especially synthetic DNA sequences. The term also captures sequences that include any of the known base analogs of DNA and RNA.

Operably linked refers to an arrangement of elements wherein the components so described are configured so as to perform their desired function. Thus, a given promoter operably linked to a coding sequence is capable of effecting the expression of the coding sequence when the proper transcription factors, etc., are present. The promoter need not be contiguous with the coding sequence, so long as it functions to direct the expression thereof. Thus, for example, intervening untranslated yet transcribed sequences can be present between the promoter sequence and the coding sequence, as can transcribed introns, and the promoter sequence can still be considered operably linked to the coding sequence.

Recombinant as used herein to describe a nucleic acid molecule means a polynucleotide of genomic, cDNA, viral, semisynthetic, or synthetic origin which, by virtue of its origin or manipulation is not associated with all or a portion of the polynucleotide with which it is associated in nature. The term recombinant as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

A control element refers to a polynucleotide sequence which aids in the expression of a coding sequence to which it is linked. The term includes promoters, transcription termination sequences, upstream regulatory domains, polyadenylation signals, untranslated regions, including 5'-UTRs (such as Exon 2 of the hCMV enhancer/promoter region 5'-UTR) and 3'-UTRs and when appropriate, leader sequences and enhancers, which collectively provide for the transcription and translation of a coding sequence in a host cell.

A promoter as used herein is a DNA regulatory region capable of binding RNA polymerase in a host cell and initiating transcription of a downstream (3' direction) coding sequence operably linked thereto. For purposes of the present invention, a promoter sequence includes the minimum number of bases or elements necessary to initiate transcription of a gene of interest at levels detectable above background. Within the promoter sequence is a transcription initiation site, as well as protein binding domains (consensus sequences) responsible for the binding of RNA polymerase. Eucaryotic promoters will often, but not always, contain 1TATAA boxes and CAAT boxes.

A control sequence directs the transcription of a coding sequence in a cell when RNA polymerase will bind the promoter sequence and transcribe the coding sequence into mRNA, which is then translated into the polypeptide encoded by the coding sequence.

A host cell is a cell which has been transformed, or is capable of transformation, by an exogenous DNA sequence.

A heterologous region of a DNA construct is an identifiable segment of DNA within or attached to another DNA molecule that is not found in association with the other molecule in nature. For example, a sequence encoding a human protein other than the immediate-early 72,000 molecular weight protein of hCMV is considered a heterologous sequence when linked to an hCMV IE1 enhancer/promoter. Similarly, a sequence encoding the immediate-early 72,000 molecular weight protein of hCMV will be considered heterologous when linked to an hCMV promoter with which it is not normally associated. Another example of a heterologous coding sequence is a construct where the coding sequence itself is not found in nature (e.g., synthetic sequences having codons different from the native gene). Allelic variation or naturally occurring mutational events do not give rise to a heterologous region of DNA, as used herein.

By selectable marker is meant a gene which confers a phenotype on a cell expressing the marker, such that the cell can be identified under appropriate conditions. Generally, a selectable marker allows selection of transected cells based on their ability to thrive in the presence or absence of a chemical or other agent that inhibits an essential cell function. Suitable markers, therefore, include genes coding for proteins which confer drug resistance or sensitivity thereto, impart color to, or change the antigenic characteristics of those cells transfected with a nucleic acid element containing the selectable marker when the cells are grown in an appropriate selective medium. For example, selectable markers include: cytotoxic markers and drug resistance markers, whereby cells are selected by their ability to grow on media containing one or more of the cytotoxins or drugs; auxotrophic markers by which cells are selected by their ability to grow on defined media with or without particular nutrients or supplements, such as thymidine and hypoxanthine; metabolic markers by which cells are selected for, e.g., their ability to grow on defined media containing the appropriate sugar as the sole carbon source, or markers which confer the ability of cells to form colored colonies on chromogenic substrates or cause cells to fluoresce. Representative selectable markers are described in more detail below.

Expression cassette or expression construct or construct refers to an assembly which is capable of directing the expression of the sequence(s) or gene(s) of interest. The expression cassette includes control elements, as described above, such as a promoter or promoter/enhancer (such as the hCMV IE1 enhancer/promoter) which is operably linked to (so as to direct transcription of) the sequence(s) or gene(s) of interest, and often includes a polyadenylation sequence as well. An expression cassette will also include an Intron A fragment as defined above and, optionally, Exon 2 of the hCMV IE1 enhancer/promoter region. Within certain embodiments of the invention, the expression cassette described herein may be contained within a plasmid construct. In addition to the components of the expression cassette, the plasmid construct may also include, one or more selectable markers, a signal which allows the plasmid construct to exist as single-stranded DNA (e.g., a M13 origin of replication), at least one multiple cloning site, and a mammalian origin of replication (e.g., a SV40 or adenovirus origin of replication).

Transformation, as used herein, refers to the insertion of an exogenous polynucleotide into a host cell, irrespective of the method used for insertion: for example, transformation by direct uptake, transfection, infection, and the like. For particular methods of transfection, see further below. The exogenous polynucleotide may be maintained as a nonintegrated vector, for example, an episome, or alternatively, may be integrated into the host genome.

By isolated is meant, when referring to a polypeptide, that the indicated molecule is separate and discrete from the whole organism with which the molecule is found in nature or is present in the substantial absence of other biological macro-molecules of the same type. The term isolated with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

Homology refers to the percent identity between two polynucleotide or two polypeptide moieties. Two DNA, or two polypeptide sequences are substantially homologous to each other when the sequences exhibit at least about 50%, preferably at least about 75%, more preferably at least about 80%-85% (80, 81, 82, 83, 84, 85%), preferably at least about 90%, and most preferably at least about 95%-98% (95, 96, 97, 98%), or more, or any integer within the range of 50% to 100%, sequence identity over a defined length of the molecules. As used herein, substantially homologous also refers to sequences showing complete identity to the specified DNA or polypeptide sequence.

Identity refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as. Atlas of Protein Sequence and Structure (National Biomedical Research Foundation. and Dayhoff 1978), which adapts the local homology algorithm of Smith and Waterman (Smith, Waterman et al. 1985) for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the Match value reflects sequence identity. Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+ PDB+GenBank CDS translations+Swiss protein+Spupdate+ PIR.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; DNA Cloning, supra; Nucleic Acid Hybridization, supra.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, COS cells, HeLa cells, baby hamster kidney cells and many others. A common, preferred bacterial host is E. coli.

Suitable vectors can be chosen or constructed, containing appropriate regulatory sequences, including promoter sequences, terminator fragments, polyadenylation sequences, enhancer sequences, marker genes and other sequences as appropriate. For further details see, for example, Molecular Cloning: a Laboratory Manual: (Sambrook and Russell 2001), or Short Protocols in Molecular Biology, eds. (Ausubel 2002). Transformation procedures depend on the host used, but are well known.

Nucleic acid for use according to the invention may be DNA or RNA, and may be single-stranded or double-stranded, cDNA, genomic DNA or wholly or partially synthetic. Double-stranded DNA is preferred.

A wide variety of bifunctional or polyfunctional cross-linking reagents, both homo- and heterofunctional, are known in the art and are commercially available (e.g. Pierce Chemical Co., Rockford, Ill.). Such cross-linking reagents may be reacted with the antigen and ligand by standard methods (e.g. according to the manufacturers instructions). Following cross-linkage, the antigen-ligand complex may be purified from unreacted antigen and ligand by standard methods (e.g., chromatography, SDS-PAGE and the like). The efficacy of chemically cross-linked compositions in stimulating intracellular signals in B cells (e.g. increased intracellular calcium concentrations) and/or modulating immune responses can be evaluated using assays, e.g. as described herein.

The administration of a recombinant vaccine may be for a prophylactic purpose (vaccination, e.g. anti-microbial) or therapeutic, e.g in immunotherapy (e.g. anti-microbial or anti-tumour). Vaccination may be used to confer on a subject protective immunity to an antigen.

In accordance with the present invention antibody production in vitro, e.g. in culture, may be stimulated. For example, B cells specific for an antigen of interest may be cultured with a stimulatory composition of the invention to stimulate production by the B cells of antibody for the antigen of interest. The antibodies produced may be isolated from the culture medium, e.g. by virtue of their binding capability for the antigen.

In a further aspect, the present invention provides a pharmaceutical composition which comprises a CeLTOS antigen/immunogen as disclosed.

Pharmaceutical compositions according to the present invention may comprise, in addition to the antigen/immunogen, a pharmaceutically acceptable excipient, carrier, vehicle, buffer, stabiliser or other materials well known to those skilled in the art. Such materials should be non-toxic and should not interfere with the efficacy of the active ingredient. The precise nature of the carrier or other material will depend on the route of administration, which will preferably be cutaneous, subcutaneous or intravenous injection, especially subcutaneous.

For parental, intravenous, cutaneous or subcutaneous injection, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required. Subcutaneous injection may be preferred route of administration.

A pharmaceutical composition in accordance with the present invention may comprise one or more additional active ingredients. For example, the composition may contain an additional agent that has immunomodulatory properties, such as a cytokine or (additional) adjuvant.

Antibodies which are specific for a target of interest may be obtained using techniques which are standard in the art. Methods of producing antibodies include immunising a mammal (eg mouse, rat, rabbit, horse, goat, sheep or monkey) with the protein or a fragment thereof, or a cell or virus which expresses the protein or fragment. Immunisation with DNA encoding a target polypeptide is also possible. Antibodies may be obtained from immunised animals using any of a variety of techniques known in the art, and screened, preferably using binding of antibody to antigen of interest. For instance, Western blotting techniques or immunoprecipitation may be used (Armitage, Fanslow et al. 1992).

As an alternative or supplement to immunizing a mammal, an antibody may be obtained from a recombinantly produced library of expressed immunoglobulin variable domains, eg using lambda bacteriophage or filamentous bacteriophage which display functional immunoglobulin binding domains on their surfaces; for instance see WO92/01047. The library may be naive, that is constructed from sequences obtained from an organism which has not been immunized with the target, or may be one constructed using sequences obtained from an organism which has been exposed to the antigen of interest (or a fragment thereof).

It is possible to take antibodies and use the techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP-A-184187, GB 2188638A or EP-A-239400. A hybridoma producing a monoclonal antibody may be subject to genetic mutation or other changes, which may or may not alter the binding specificity of antibodies produced.

It may be desirable to humanize non-human (eg murine) antibodies to provide antibodies having the antigen binding properties of the non-human antibody, while minimizing the immunogenic response of the antibodies, e.g. when they are used in human therapy. Thus, humanized antibodies comprise framework regions derived from human immunoglobulins (acceptor antibody) in which residues from one or more complementary determining regions (CDR's) are replaced by residues from CDR's of a non-human species (donor antibody) such as mouse, rat or rabbit antibody having the desired properties, eg specificity, affinity or capacity. Some of the framework residues of the human antibody may also be replaced by corresponding non-human residues, or by residues not present in either donor or acceptor antibodies. These modifications are made to the further refine and optimize the properties of the antibody.

So-called phage display may also be used in humanising antibodies; see e.g. WO93/06213.

Example 1

We immunized Balb/c and ICR mice with either the recombinant protein adjuvanted with MONTANIDE ISA-720 ™ (A.L.A. Intermountain, 3725 E. Washington Street, Phoenix, Ariz. 85034). or with a pCI-TPA plasmid encoding the *P. berghei* CelTOS using an epidermal delivery by gene-gun to characterize their abilities to induce protective responses against a homologous *P. berghei* challenge. Humoral and cellular immune responses induced by either protein or plasmid immunizations were assessed in an effort to establish immune correlates. Results of the studies are show in FIGS. 1 through 3. The finding of arrested hepatocytic invasion by inducing immunity to target antigens involved in sporozoite traversal or motility shows the enablement of the embodiment of the invention wherein CelTOS is utilized as a vaccine component.

Vaccination with PfCelTOS induced responses that protected mice against heterologous challenge (*P. berghei*). The MONTANIDE ISA 720™ adjuvant used for induction of immune responses is commercially available from Seppic, Inc. (A.L.A. Intermountain, 3725 E. Washington Street, Phoenix, Ariz. 85034). The recombinant protein *P. falciparum* CelTOS was developed solely by investigators in Division of MVD at WRAIR through funding from U.S. Agency for International Development (Project Number 936-6001, Award Number AAG-P-00-98-00006, Award Number AAG-P-00-98-00005), and by the United States Army Medical Research and Materiel Command. This malaria vaccine antigen can be used with other for human use adjuvants to induce appropriate immune responses.

Figure 14A:
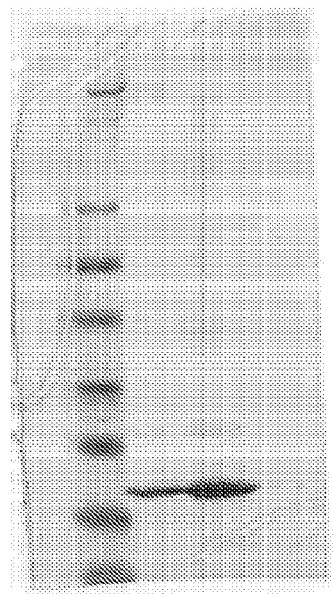
Figure 14B:
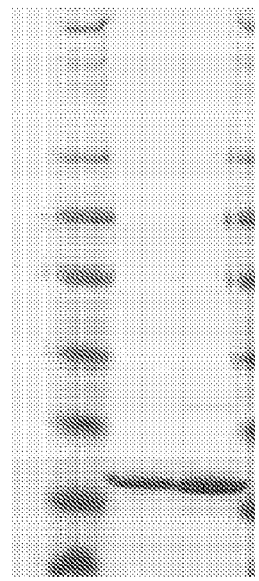

As shown in FIG. 4, the nucleotide sequence of the *Plasmodium* CelTOS is re-coded by the codon harmonization disclosed in published U.S. patent application Ser. No. 10/677,641 to Kincaid et al. The codons are harmonized to optimize for high levels of soluble protein expression in the heterologous system, i.e. *E. coli*—see FIGS. 14A and 14B. The FASTA sequence for wild-type *Plasmodium* CelTOS is:

```
>gi|23496693|gb|AAN36249.1| CelTOS, putative
[Plasmodium falciparum 3D7]
                                      (SEQ. ID. NO. 4)
MNALRRLPVICSFLVFLVFSNVLCFRGNNGHNSSSSLYNGSQFIEQLNNS

FTSAFLESQSMNKIGDDLAETISNELVSVLQKNSPTFLESSFDIKSEVKK

HAKSMLKELIKVGLPSFENLVAENVKPPKVDPATYGIIVPVLTSLFNKVE

TAVGAKVSDEIWNYNSPDVSESEESLSDDFFD.
```

Figure 11B:
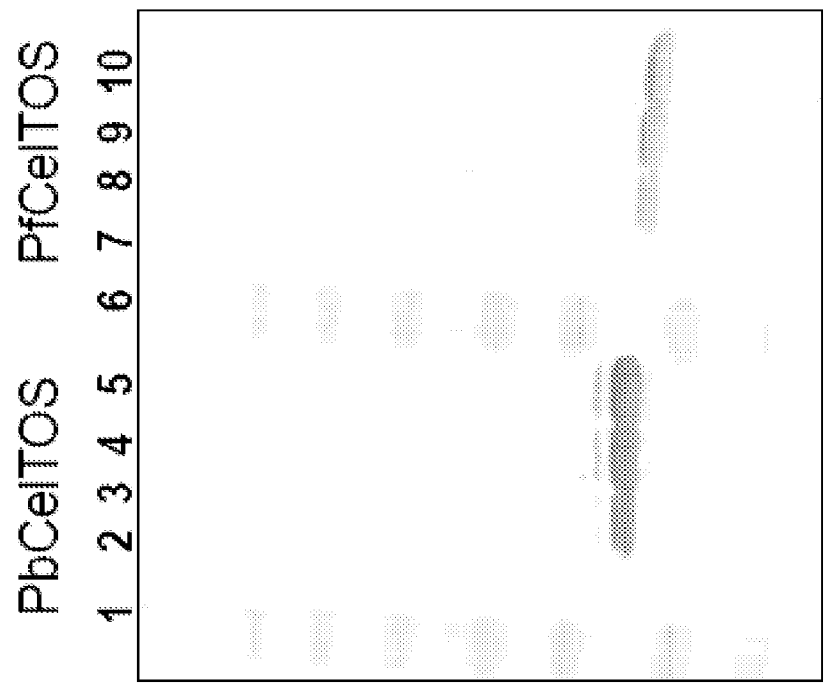
Figure 11A:
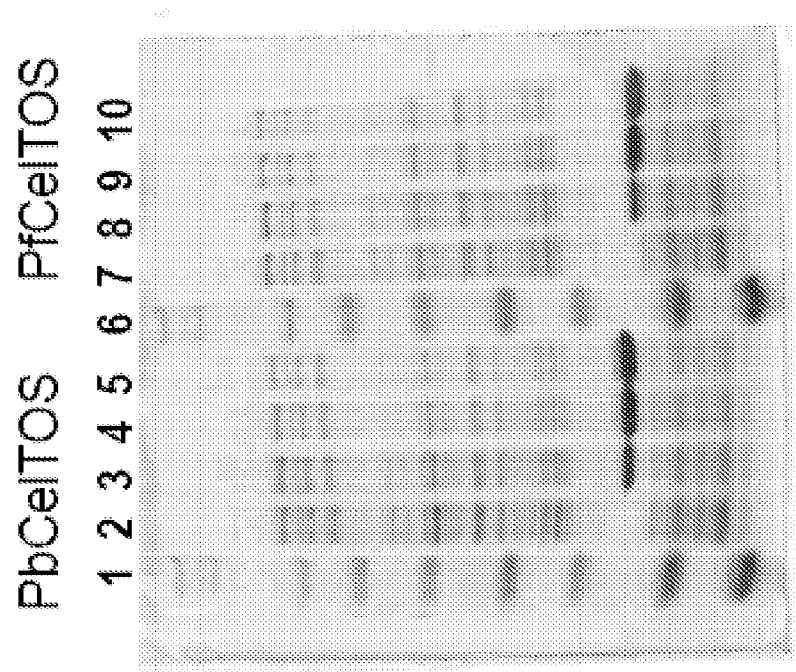
Figure 13:
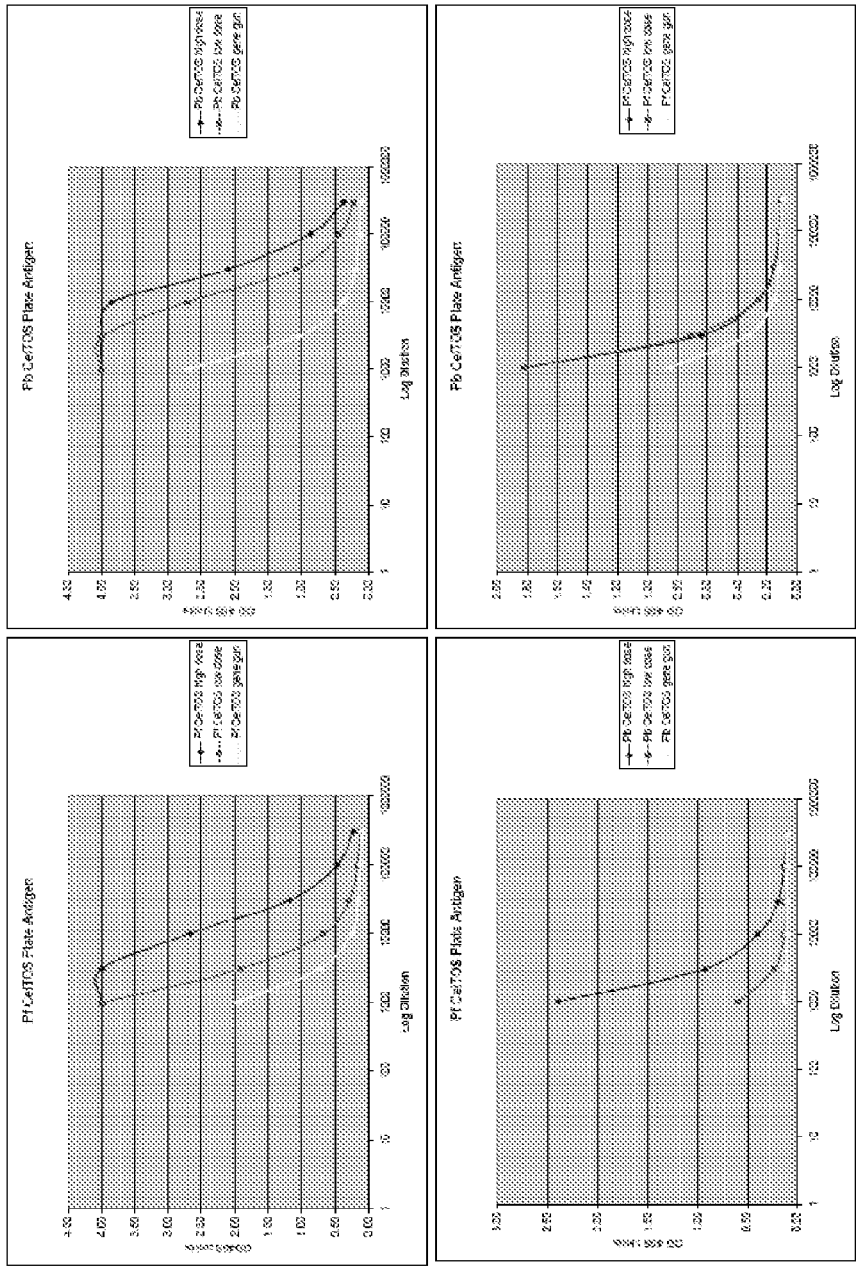

The CelTOS antigen was constructed in recombinant plasmids as shown in FIGS. 7-10. Both PbCelTOS and PfCelTOS recombinants demonstrated expression of the CelTOS antigen as shown in FIGS. 11A and 11B. As the antigen is expressed in prokaryotic cells, i.e. *E. coli* no post-translational modification of N-glycosylation on the expressed protein which occurs such as in eukaryotic expression systems. It is know that *P. falciparum* malaria proteins are not N-glycosylated. N-glycosylation may lead to changes in the protein folding and thus structure and may affect the induction of appropriate immune responses. It is known that the *P. falciparum* CelTOS protein has 2 likely N-glycosylation sites and a third probable N-glycosylation site. Accordingly, the present invention overcomes the above-described shortcomings of the prior art.

We conclude from Study #1 that recombinant protein PfCelTOS is able to induce a protective response against heterologous challenge with *P. berghei* sporozoites (4000 subcutaneous). At the same time, the PbCelTOS model antigen protected against homologous challenge as well (see Table 1 at FIG. 1). Protective responses were also induced in out-bred ICR mice vaccinated with PfCelTOS (Table 2, ICR mice at FIG. 2) and challenged with 15000 *P. berghei* sporozoites. Repeat dosing in BalbC mice (see Table 2—BalbC at FIG. 3), with PbCelTOS again showed that in this mouse model, CelTOS protected mice against a virulent challenge. These results support the use of PfCelTOS as a transmission blocking (anti-ookinetestage) and anti-infectivity (anti-sporozoite stage) malaria vaccine candidate.

Example 2

Supporting Data Provided for the Ability of Recombinant PfCelTOS Vaccine to Induce a Functional Activity Against Sporozoites Motility assays: IFA slides (Cell Point, Gaithersburg, Md.) were pre-coated with RPMI-1640 (Invitrogen, Carlsbad, Calif.) containing 3% BSA (Sigma) for 15 min at 37° C. After removing the media, 10,000 sporozoites/well were added and incubated for 1 hr in a humidified chamber at 37° C. Slides and the deposited protein trails were fixed using 4% paraformaldehyde (10 min, RT). Spots were blocked with PBS containing 10% FBS for 45 min at 37° C. and then incubated with anti-PfCSP mAb (216.5G10 or 8C10 or 2G3 strains) for 45 min at 37° C. Goat-anti-mouse-IgG-FITC was added (1:100 dilution, Southern Biotech) to visualize the trails. Finally, slides were coverslipped using Fluoromount mounting media and microscopy performed (Olympus BX41, 1000× magnification).

Sporozoite motility is an indirect measure of the viability and health of the parasites, therefore the motility assay can serve as a functional readout to determine whether the presence of anti-CelTOS antibodies can inhibit the motility of sporozoites in a gliding motility assay. To this end, mature sporozoites (day 18-20) from salivary glands were dissected and incubated for 15 min with either control serum or various other antisera. After the pre-incubation, the sporozoites were plated without washing onto glass slides and incubated for 1 hr at 37° C. The incubation of sporozoites with control mouse serum (either pre-immune or serum from adjuvant-injected mice) resulted in the deposition of CSP; CSP trails were typically extensive and allowed the ability to establish an overall fitness of the sporozoites (see FIG. 15A). Similarly, the presence of CSP-specific mAbs resulted in extensive trails that often were more pronounced and stronger than for control cultures (see FIG. 15B). In contrast, the presence of anti-PfCelTOS specific antisera led to either much shorter trails or no trails at all (see FIG. 15C).

This experiment how a humoral anti-CeltTOS response can confer protection in a live host.

While a specific embodiment of the invention has been shown and described in detail to illustrate the application of the principles of the invention, it will be understood that the invention may be embodied otherwise without departing from such principles.

REFERENCES (The contents of each of which, and the contents of every other publication, including patent publications such as PCT International Patent Publications, being incorporated herein by this reference.)

Armitage, R. J., W. C. Fanslow, et al. (1992). "Molecular and biological characterization of a murine ligand for CD40." Nature 357(6373): 80-2.

Ausubel, F. M. (2002). Short protocols in molecular biology: a compendium of methods from Current protocols in molecular biology. New York, Wiley.

Bruna-Romero, O., G. Gonzalez-Aseguinolaza, et al. (2001). "Complete, long-lasting protection against malaria of mice primed and boosted with two distinct viral vectors expressing the same plasmodial antigen." Proc Natl Acad Sci USA 98(20): 11491-6.

Gait, M. J. (1984). Oligonucleotide synthesis: a practical approach. Oxford [Oxfordshire]; Washington, D.C., IRL Press.

Glover, D. M. and B. D. Hames (1994). DNA cloning: a practical approach. Oxford; New York, IRL Press.

Kariu, T., T. Ishino, et al. (2006). "CelTOS, a novel malarial protein that mediates transmission to mosquito and vertebrate hosts." Mol Microbiol 59(5): 1369-79.

National Biomedical Research Foundation. and M. O. Dayhoff (1978). Protein segment dictionary 78: from the Atlas of protein sequence and structure, volume 5, and supplements 1, 2, and 3. Silver Spring, Md.; Washington, D.C., National Biomedical Research Foundation; Georgetown University Medical Center.

Perbal, B. V. (1988). A practical guide to molecular cloning. New York, Wiley.

Sambrook, J. and D. W. Russell (2001). Molecular cloning: a laboratory manual. Cold Spring Harbor, N.Y., Cold Spring Harbor Laboratory Press.

Sambrook, J. and D. W. Russell (2006). The condensed protocols from Molecular cloning: a laboratory manual. Cold Spring Harbor, N.Y., Cold Spring Harbor Laboratory Press.

Smith, T. F., M. S. Waterman, et al. (1985). "The statistical distribution of nucleic acid similarities." Nucleic Acids Res 13(2): 645-56.

The invention claimed is:

1. A synthetic CelTOS polypeptide, said polypeptide encoded by the synthetic nucleotide sequence identified in SEQ ID NO:1.

2. An immunogenic composition comprising the synthetic CelTOS polypeptide of claim 1.

3. The synthetic polypeptide of claim 1, wherein said protein is recombinantly expressed with no post-translational N-glycosylation.

4. The immunogenic composition of claim 2 further comprising an adjuvant.

5. A malaria vaccine comprising the synthetic CelTOS polypeptide of claim 1.

6. The vaccine of claim 5 further comprising an adjuvant.

7. A method for inducing an immune response to *Plasmodium* malaria in a mammal, comprising administering a composition comprising the synthetic CelTOS polypeptide of claim 1 in an amount effective induce an immune response.

8. The method according to claim 7 wherein the composition further comprises an adjuvant.

9. A method for detecting malaria antibodies in a biological sample, comprising contacting the biological sample with a polypeptide according to claim 1 such that a complex forms between the polypeptide and malaria antibodies in said sample, and detecting the presence or absence of said complex, such that the presence of said complex indicates the presence of malaria antibodies in said sample.

10. A kit for detection of malaria antibodies in a biological sample, comprising the synthetic polypeptide of claim 1, a buffer or components necessary for producing the buffer, enabling a binding reaction between the polypeptide and malaria antibodies present in the biological sample, and a means for detecting complexes formed in the binding reaction.

* * * * *